United States Patent
Nielsen et al.

(10) Patent No.: US 9,623,188 B2
(45) Date of Patent: Apr. 18, 2017

(54) DRUG DELIVERY INJECTION PEN WITH ADD-ON DOSE CAPTURING AND DISPLAY MODULE

(75) Inventors: Ole Christian Nielsen, Hilleroed (DK); Morten Soerensen, Ballerup (DK); John Oestergaard Madsen, Roedovre (DK); Claus Tipsmark, Humlebaek (DK)

(73) Assignee: Novo Nordisk A/S, Bagsvaerd (DK)

( * ) Notice: Subject to any disclaimer, the term of this patent is extended or adjusted under 35 U.S.C. 154(b) by 221 days.

(21) Appl. No.: 14/127,363

(22) PCT Filed: Jul. 9, 2012

(86) PCT No.: PCT/EP2012/063350
§ 371 (c)(1),
(2), (4) Date: Mar. 17, 2014

(87) PCT Pub. No.: WO2013/004844
PCT Pub. Date: Jan. 10, 2013

(65) Prior Publication Data
US 2014/0194825 A1    Jul. 10, 2014

Related U.S. Application Data

(60) Provisional application No. 61/507,222, filed on Jul. 13, 2011.

(30) Foreign Application Priority Data

Jul. 7, 2011   (EP) ...................................... 11173080

(51) Int. Cl.
*A61M 5/315*    (2006.01)
*A61M 5/24*     (2006.01)
(Continued)

(52) U.S. Cl.
CPC .......... *A61M 5/31535* (2013.01); *A61M 5/24* (2013.01); *A61M 5/31525* (2013.01);
(Continued)

(58) Field of Classification Search
CPC ................ A61M 5/24; A61M 5/31525; A61M 5/31535; A61M 5/3129;
(Continued)

(56) References Cited

U.S. PATENT DOCUMENTS

| | | | |
|---|---|---|---|
| 5,383,865 A | 1/1995 | Michel | |
| 5,830,152 A | 11/1998 | Tao | |

(Continued)

FOREIGN PATENT DOCUMENTS

| | | | | |
|---|---|---|---|---|
| DE | EP 2060284 A1 | * | 5/2009 | .......... A61M 5/1413 |
| DE | 102009003721 A1 | | 10/2010 | |
| EP | 2060284 A1 | | 5/2009 | |
| WO | 2006/086733 A2 | | 8/2006 | |
| WO | 2006/134173 A2 | | 12/2006 | |
| WO | 2007/003898 A1 | | 1/2007 | |

(Continued)

*Primary Examiner* — Kevin C Sirmons
*Assistant Examiner* — Amber Stiles
(74) *Attorney, Agent, or Firm* — Wesley Nicolas (57) ABSTRACT

Drug injection device (400) comprising expelling means for expelling an amount of drug from a reservoir, the expelling means comprising setting means (411) allowing a user to set a dose to be expelled, and actuation means (413) for releasing the drug expelling means to expel the set dose. The actuation means comprises an actuation member adapted to be moved between an initial position, an intermediate position, and an actuated position in which the expelling means is actuated to expel the set dose. The device further comprises an electronically controlled capturing system (420) for capturing data representing the amount of drug expelled from the reservoir by the expelling means, and switch means for starting initialization of the capturing system when the actuation member is moved to its intermediate position.

15 Claims, 9 Drawing Sheets

(51) Int. Cl.
*G06F 19/00* (2011.01)
*A61M 5/31* (2006.01)
(52) U.S. Cl.
CPC ...... *G06F 19/3406* (2013.01); *G06F 19/3456* (2013.01); *G06F 19/3468* (2013.01); *G06F 19/3487* (2013.01); *A61M 5/3129* (2013.01); *A61M 2005/3126* (2013.01); *A61M 2005/3142* (2013.01); *A61M 2205/3306* (2013.01); *A61M 2205/50* (2013.01); *A61M 2205/502* (2013.01); *A61M 2205/52* (2013.01); *A61M 2205/8212* (2013.01); *A61M 2209/04* (2013.01)
(58) Field of Classification Search
CPC .. A61M 2005/3126; A61M 2005/3142; A61M 2205/3306; A61M 2205/50; A61M 2205/502; A61M 2205/52; A61M 2205/8212; A61M 2209/04; G06F 19/3487; G06F 19/3456; G06F 19/3468; G06F 19/3406
See application file for complete search history.

(56) References Cited

U.S. PATENT DOCUMENTS

| | | | |
|---|---|---|---|
| 6,482,185 | B1 | 11/2002 | Hartmann |
| 6,585,698 | B1 * | 7/2003 | Packman ................ A61M 5/24 |
| | | | 604/207 |
| 2008/0306434 | A1 | 12/2008 | Dobbles et al. |
| 2009/0318865 | A1 | 12/2009 | Moller et al. |
| 2014/0194826 | A1 | 7/2014 | Nielsen et al. |

FOREIGN PATENT DOCUMENTS

| | | | | |
|---|---|---|---|---|
| WO | 2010/052275 | A2 | 5/2010 | |
| WO | 2010/098927 | A1 | 9/2010 | |
| WO | 2010/098928 | A1 | 9/2010 | |
| WO | 2010/098929 | A1 | 9/2010 | |
| WO | WO 2010098928 | A1 * | 9/2010 | ............... A61M 5/24 |
| WO | WO 2010098931 | A1 * | 9/2010 | ............... A61M 5/24 |
| WO | 2010/128493 | A2 | 11/2010 | |
| WO | 2012/166622 | A1 | 12/2012 | |

* cited by examiner

DRUG DELIVERY INJECTION PEN WITH ADD-ON DOSE CAPTURING AND DISPLAY MODULE

CROSS-REFERENCE TO RELATED APPLICATIONS

This application is a 35 U.S.C. §371 National Stage application of International Application PCT/EP2012/063350 (WO 2013/004844), filed Jul. 9, 2012, which claimed priority of European Patent Application 11173080.0, filed Jul. 7, 2011; this application claims priority under 35 U.S.C. §119 of U.S. Provisional Application 61/507,222; filed Jul. 13, 2011.

The present invention relates to a system for capturing drug delivery dose data. Especially, the invention addresses the issue of generating a triggering or initialization signal for an electronic data capturing system.

BACKGROUND OF THE INVENTION

In the disclosure of the present invention reference is mostly made to the treatment of diabetes by delivery of insulin, however, this is only an exemplary use of the present invention.

Drug Injection devices have greatly improved the lives of patients who must self-administer drugs and biological agents. Drug Injection devices may take many forms, including simple disposable devices that are little more than an ampoule with an injection means or they may be durable devices adapted to be used with pre-filled cartridges. Regardless of their form and type, they have proven to be great aids in assisting patients to self-administer injectable drugs and biological agents. They also greatly assist care givers in administering injectable medicines to those incapable of performing self-injections.

Performing the necessary insulin injection at the right time and in the right size is essential for managing diabetes, i.e. compliance with the specified insulin regimen is important. In order to make it possible for medical personnel to determine the effectiveness of a prescribed dosage pattern, diabetes patients are encouraged to keep a log of the size and time of each injection. However, such logs are normally kept in handwritten notebooks, from the logged information may not be easily uploaded to a computer for data processing. Furthermore, as only events, which are noted by the patient, are logged, the note book system requires that the patient remembers to log each injection, if the logged information is to have any value in the treatment of the patient's disease. A missing or erroneous record in the log results in a misleading picture of the injection history and thus a misleading basis for the medical personnel's decision making with respect to future medication. Accordingly, it may be desirable to automate the logging of ejection information from medication delivery systems.

Though some injection devices integrate this monitoring/acquisition mechanism into the device itself, e.g. as disclosed in US 2009/0318865 and WO 2010/052275, most devices of today are without it. The most widely used devices are purely mechanical devices either durable or prefilled. The latter devices are to be discarded after being emptied and so inexpensive that it is not cost-effective to build-in electronic data acquisition functionality in the device it-self. Correspondingly, data acquisition/monitoring functionality have been proposed to be provided in a separate device to be put on or in the injection device, i.e. some kind of accessory e.g. an add-on module to the injection device.

For example, WO 2010/098927 discloses a medical module which is configured to be attached to a drug delivery pen, the module being adapted to detect and store selected and ejected dosages as well as other data. Further arrangements adapted to capture dose data are known from WO 2010/128493, EP 2 060 284 and WO 2010/052275.

Having regard to the above, it is an object of the present invention to provide systems and methods supporting simple and reliable yet cost- and energy-effective detection and storage of dose data related to use of a drug delivery device.

DISCLOSURE OF THE INVENTION

In the disclosure of the present invention, embodiments and aspects will be described which will address one or more of the above objects or which will address objects apparent from the below disclosure as well as from the description of exemplary embodiments.

Thus, in a first aspect of the invention a drug delivery system is provided, comprising expelling means for expelling an amount of drug from a reservoir, the expelling means comprising (a) setting means allowing a user to set a dose amount of drug to be expelled, and (b) actuation means for releasing or driving the drug expelling means to expel the set dose amount. The system further comprises an electronically controlled capturing system for capturing data representing a property related to the amount of drug expelled from a reservoir by the expelling means, and switch means for starting initialization of the capturing system. The actuation means comprises an actuation member adapted to be moved between (i) an initial position, (ii) an intermediate position in which the switch means is actuated to start initialization of the capturing system, and (iii) an actuated position in which the expelling means is actuated to expel the set dose. By this arrangement the capturing system is allowed to initialize during the actuation member's movement between the intermediate position and the actuated position.

When providing a data capture system, it should be secured that the system is operational in good time before the system shall make its data acquisition (of e.g. out-dosing amount and out-dosing time) in order to get the electronics ready for the measurement(s). Initialization may include power-up time for the electronics of a fully or partly dormant system, the time for initializing the electronics or the necessary time for the electronics to make a reliable measuring/data acquisition. By the above arrangement an energy-effective system is provided which is energized just prior to out-dosing (i.e. when the user actuates the actuation member to its intermediate position), yet sufficiently early to allow the electronic data capture system to capture data prior to the expelling means being released or driven.

As stated, the switch means is actuated when the actuation member is moved to its intermediate position, however, actuation of the switch means may take place directly, i.e. by the actuation member or a component attached thereto, or indirectly, i.e. by a component moved directly or indirectly by the actuation member.

The drug delivery system may comprise a first indicator portion which moves when the actuation member is moved (e.g. linearly) between its initial and intermediate position. The switch means may comprise e.g. optical sensor means or a mechanical switch adapted to detect when the first indicator portion is moved in response to the actuation member being moved from its initial to its intermediate position.

The drug delivery system may comprise an identifier associated with a second indicator portion which moves (e.g. rotationally) during drug expelling and represents a property related to the amount of drug expelled from a reservoir by the expelling means, the detection means being adapted to capture the identifier. The detection means may be in the form of optical sensor means adapted to capture values represented by the identifier.

Other means for communicating and capturing data related to dose size may be implemented. For example, the pen may be provided with electronic means generating a wireless signal to be captured by the capturing system, it may be provided with magnetic means or the pen may produce an audible signal to be captured by the capturing system.

In an exemplary embodiment the drug delivery system comprises a drug delivery unit and a data capture unit releasably attachable to each other, the drug delivery unit comprising the drug expelling means, the dose setting means, and the actuation means, whereas the data capture unit comprises the electronically controlled capturing system, and the switch means.

In a second aspect of the invention a drug delivery system is provided, comprising drug expelling means for expelling an amount of drug from a reservoir, comprising (i) setting means allowing a user to set a dose amount of drug to be expelled, and (ii) actuation means for releasing or driving the drug expelling means to expel the set dose amount. The delivery system further comprises an electronically controlled capturing system for capturing data representing a property related to an amount of drug expelled by the expelling means, an identifier associated with a member which moves during drug expelling and represents a property related to the amount of drug expelled from a reservoir by the expelling means, the capturing system being adapted to capture the identifier. The delivery system further comprises switch means for starting initialization of the capturing system, the switch means being actuated as the identifier starts to move when the drug expelling means has been released or starts to be driven by the actuation means. Dose data representing a property related to the amount of drug expelled from the reservoir by the expelling means is captured when the set dose amount has been expelled or expelling has stopped for predetermined amount of time. In this way the identifier is used to serve dual purposes.

In a further aspect a drug delivery system is provided comprising a drug delivery unit comprising drug expelling means for expelling an amount of drug from a reservoir, the drug expelting means comprising setting means allowing a user to set a dose amount to be expelled from a drug reservoir, and actuation means for releasing or driving the drug expelling means to expel the set dose amount. The drug delivery system further comprises a data capture unit releasably attachable to the drug delivery unit (e.g. of the type described above), the data capture unit comprising an electronically controlled capturing system for capturing data representing a property related to the amount of drug expelled from the reservoir by the expelling means, and transmission means for transmitting, e.g. wirelessly, the captured data, the drug delivery system further comprising a cap unit releasably mountable to the drug delivery unit, the cap unit comprising receiving means for receiving, e.g. wirelessly, the captured data from the data capture unit, and display means adapted to display a value corresponding to the captured data. By this arrangement a simpler data capture unit can be provided in case the display of another unit can be used. In an exemplary embodiment the cap unit comprises a BGM. The cap display may also be in the form of the below-described tag device receiving RF data input from a data capture unit.

For the above-described aspects and embodiments, the drug delivery system may be pre-filled comprising a drug reservoir not intended to be replaced after it has been emptied, or the system may be configured to receive a drug reservoir in the form of a replaceable drug cartridge, e.g. comprising a cartridge holder.

In a yet further aspect a drug delivery system is provided comprising a main portion comprising drug expelling means for expelling drug from a reservoir through an outlet. The drug delivery system further comprises a self-contained tag device adapted to display information, the tag device comprising a display, receiving means adapted to receive data from an external source, and controller means for controlling the display to display information in accordance with the received data.

In exemplary embodiments the tag device comprises no battery (i.e. electrochemical cell(s)) with the receiving means being adapted to receive a RF signal wherein the controller means is energized by received RF signals. The display may be based on e-paper technology (e.g. an electrical bi-stable display) and be adapted to display a numerical value representing a recommended dose size of drug to be expelled from the reservoir. The tag device may be in the form of a flexible foil member attached to e.g. a curved surface of the main portion of the drug delivery system. The display of the tag device may cover at least 50% of its surface area. The drug delivery system may comprise a cap portion releasably mountable to the main portion and adapted to cover the outlet in a mounted position, the tag device being in the form of a flexible foil member attached to e.g. a curved surface of the cap portion. The system may be adapted to communicate with external controller means adapted to transmit appearance data to be received by the tag device receiving means, the appearance data providing that a majority of the display is controlled to display e.g. a substantially uniform colour or a pattern, this indicating the type of drug contained in the reservoir, e.g. green for long-acting and orange for fast-acting insulin. In addition or alternatively the display may be used to personalize the device, e.g. cartoon figures for children.

As used herein, the term "insulin" is meant to encompass any drug-containing flowable medicine capable of being passed through a delivery means such as a cannula or hollow needle in a controlled manner, such as a liquid, solution, gel or fine suspension, and which has a blood glucose controlling effect, e.g. human insulin and analogues thereof as well as non-insulins such as GLP-1 and analogues thereof. In the description of the exemplary embodiments reference will be made to the use of insulin.

BRIEF DESCRIPTION OF THE DRAWINGS

In the following the invention will be further described with reference to the drawings, wherein.

In the figures like structures are mainly identified by like reference numerals.

DESCRIPTION OF EXEMPLARY EMBODIMENTS

When in the following terms such as "upper" and "lower", "right" and "left", "horizontal" and "vertical" or similar relative expressions are used, these only refer to the appended figures and not necessarily to an actual situation of use. The shown figures are schematic representations for which reason the configuration of the different structures as well as their relative dimensions are intended to serve illustrative purposes only.

Figure 1:
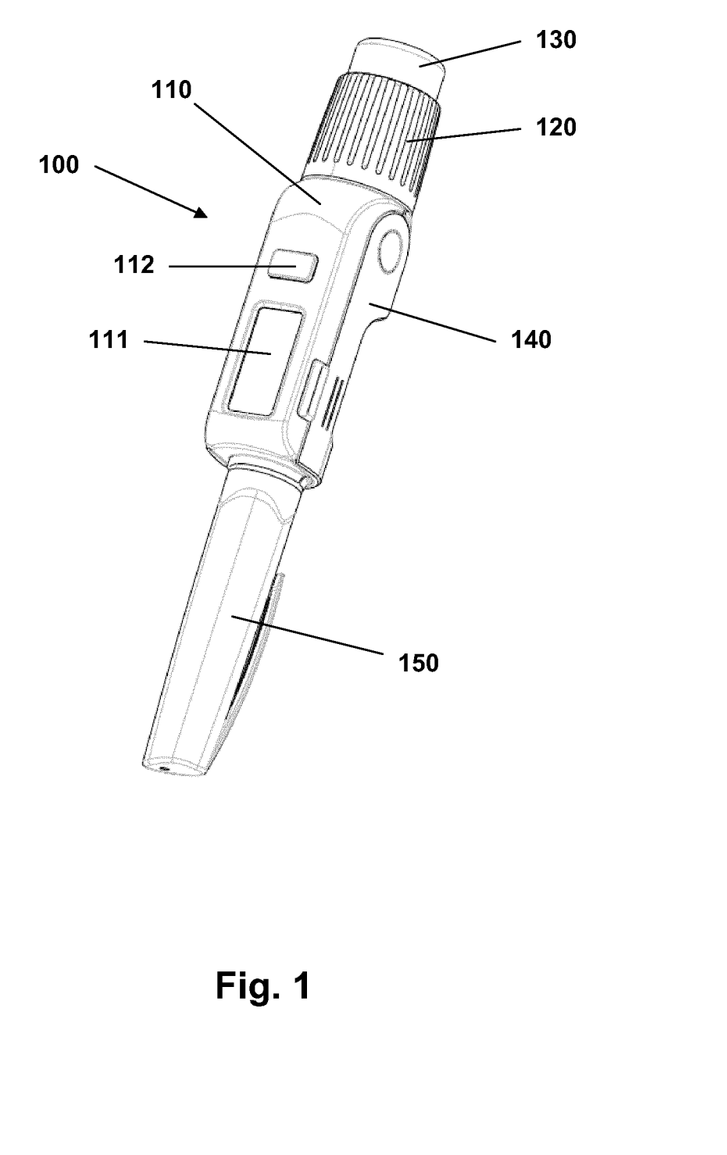
FIG. 1 shows a pen-type drug delivery device in combination with an add-on dose logging module.

FIG. 1 shows an embodiment of a drug delivery system comprising a pen-formed drug delivery unit and a data capture unit releasably attachable to each other, however, the figure could also represent a drug delivery device comprising integrated data capture means. The drug delivery unit per se could be of any desirable design providing the necessary input to the data capture unit, however, the shown embodiment represents the type of pen in which a spring is loaded during setting of a dose, this allowing spring-driven drug expelling when the set and loaded mechanism is released by the user, this allowing a design in which the release (or actuation) button is axially stationary during dose setting. A more detailed description of such a pen can be found in e.g. US 2009/054839, US 2008/306446 and US 2008/234634 which are hereby incorporated by reference.

More specifically, such a drug delivery device of the pen type comprises a proximal part having a mainly cylindrical housing portion with an expelling mechanism and a distal portion comprising a drug cartridge with an axially moveable piston driven by the expelling mechanism. The pen comprises a rotatable dose setting ring member allowing a user to set and adjust (i.e. dial-up and dial-down) a variable dose size of given increments (e.g. 1 IU insulin) to be expelled from the cartridge, the actual dose size (e.g. 25 IU insulin) being indicated by numbers shown in a window, the numbers being arranged on a rotating dose drum member. The maximum amount of drug that can be delivered during one out-dosing is defined by the injection device. For example the injection device may deliver variable dose amounts during one out-dosing between 1 IU insulin and 80 IU insulin. A push button is arranged at the proximal end and adapted to release the expelling mechanism when pushed distally by the user.

As the mechanism is released the set dose will be expelled from the cartridge and the dose drum will correspondingly rotate back towards its initial zero position. If the mechanism is designed to stop expelling when the user stops pushing the release button, the number display in the window will show the portion of the dose (e.g. the numbers of units) not yet expelled, e.g. 10 units of insulin.

Based on a drug delivery pen of the type described above FIG. 1 shows an embodiment of a drug delivery system 100 comprising a pen-formed drug delivery unit and a data capture uni 110 the units being releasably attachable to each other. The system comprises a rotatable dose setting member 120 and a proximally arranged release button 130 adapted to be moved between an initial position, an intermediate position, and an actuated position in which the expelling means is actuated to expel the set dose. The distal reservoir part of the drug delivery device is covered by a cap member 150. The data capture unit 110 comprises electronic detection means for capturing data representing a property related to the amount of drug expelled from the reservoir by the expelling means (see below), and switch means for initiating data capture, the switch means being actuated when the release button is moved from its initial to its intermediate position. The data capture unit also comprises a display 111 adapted to show e.g. time and dose size for the last expelling action, as well as a key 112 allowing a user to e.g. toggle between a number of recent time-dose logs. The data capture unit may further be provided with an output port for wired or wireless upload of data to an external device, e.g. to the users smartphone or a doctors personal computer.

Based on the above pen design, an electronic data acquisition system could be based on the following concept: To save energy the system is dormant during non-use of the device as well as during setting of the dose. When the dose is thus set and the user actuates the release button this indicates to the system that the set dose is the actual dose to be captured. However, depending on the principle used to capture information about the set dose, the system may need time to "wake up" and capture dose information before the information "is gone", i.e. the only information representing the set (and expelled) dose is the position of mechanical components, e.g. the dose drum. This would for example be the case in a system based on optical detection of information arranged on member rotating during out-dosing (see below).

In a straight-forward application of such a system onto a pen device design of the above-described type, the wake-up would have to take place during the time of travel for the release button between its initial position and the position in which the expelling mechanism is released, i.e. given such a travel is provided.

Figure 2A:
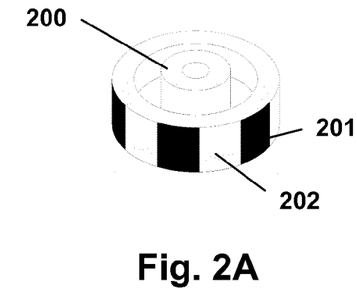
FIGS. 2A and 2B show in a schematic representation a first embodiment of an encoder/decoder system.
Figure 2B:
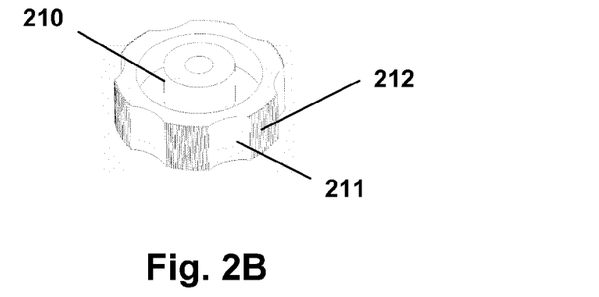
Figure 3A:
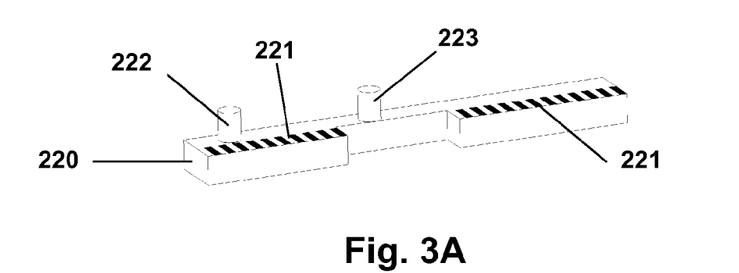
FIGS. 3A and 3B show in a schematic representation a further embodiment of an encoder/decoder system.
Figure 3B:
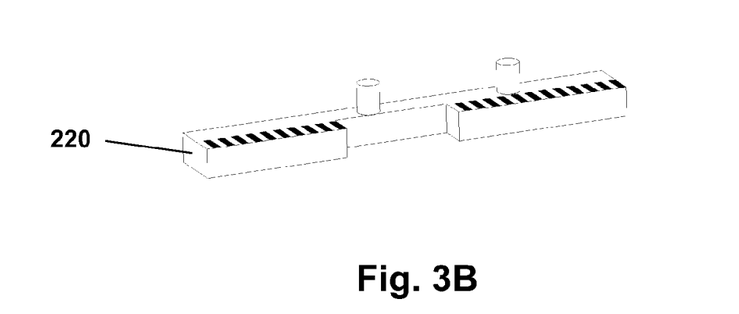
Figures 4A, 4B:
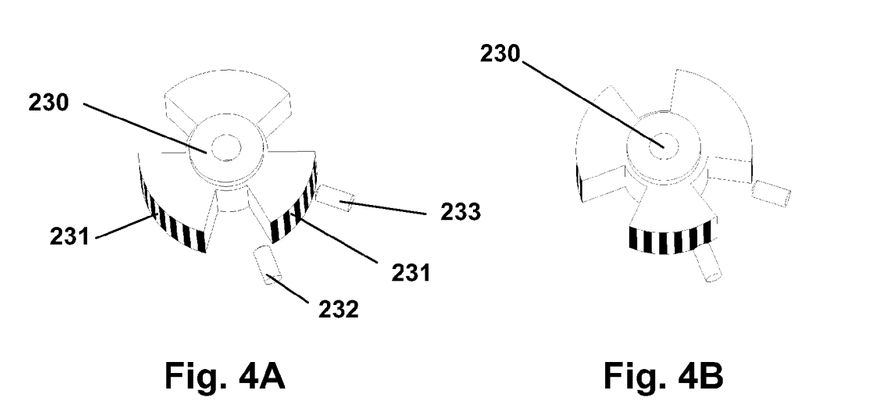
FIGS. 4A and 4B show in a schematic representation a further embodiment of an encoder/decoder system.

With reference to FIGS. 2-4 different principles for providing the switch actuation as well as the dose-related data capture will be described. More specifically, the described embodiments are primarily based on encoder/decoder systems that acquire information indicative of out-dosed amounts of drug from an injection device by means of optical detection of a code pattern on a moving part. Alternatively the same movements could be detected by means of other detection principles such as galvanic contacts, induction, capacitive coupling or magnetic field. The moving part may be a part of the out-dosing mechanism in the injection device itself, or a part in physical connection with a moving part in the out-dosing mechanism in the injection device (e.g. a mechanical or magnetic connection). The position of the moving part is related to the out-dosed amount.

The optical detector/decoder may be either integrated in the injection device itself, or arranged in an add-on device to be mounted on or in the injection device. The following description of exemplary embodiments is based on a system where the optical detector is part of an add-on device to be mounted on or in an injection device, however, the same principles could be incorporated in an integrated system.

The optical detector/decoder is designed to be able to read a code pattern (or identifier) on a moving part. The position of the moving part is related to the amount of drug being out-dosed from the device, either by being an integrated part of the out-dosing mechanism in the injection device itself, or by having a physical connection with a moving part in the out-dosing mechanism in the injection device.

The optical detector is arranged in a position relative to the moving part with the code pattern, where its field of view contains a portion of the code pattern. When out-dosing from the injection device is performed one or more elements of the internal out-dosing mechanism in the injection device is moved (or translated). When elements of the out-dosing mechanism in the injection device move this will result in a related movement of the code pattern detectable by the optical detector/decoder. Hence the part of the code pattern that is in the field of view of the optical detector changes as a consequence of the out-dosing. Since the code pattern is designed to be interpreted by the optical detector/decoder the changes of the code pattern in the field of view of the optical detector can be used to derive the position of the moving part when out-dosing starts and when out-dosing stops (and optionally during the out-dosing). Hence the out-dosing amount can be calculated and subsequently stored and/or communicated by the data acquisition system. The movement of the moving part with the code pattern may be rotational (around one or more axes), linear (in one or more directions) or a combination hereof.

The code pattern may be either a discrete code (e.g. a binary code), where the code pattern changes instantly for each increment, or it may be an analogue (non-discrete) continuously changing code pattern (e.g. a grey scale code or a colour code, that changes floatingly from one tone/colour to another tone/colour). The following description of exemplary embodiments is based on a discrete binary code, where the values (0 or 1) are detected based on the intensity of light that reaches the optical detector/decoder. By using more than one optical or binary type detector or by separating the field of view of a single optical detector a code value with more than one bit can be applied. If the code is a one bit code, the optical detector must read the code value on the moving part with a time between readings that is fast enough to safely detect every time the code value changes (e.g. each out-dosing increment) during the movement of the moving part. If the code has more bits the time between readings can be prolonged and/or a system that is more robust towards e.g. tolerances may be designed. If the code has e.g. 7 bits a total of 128 different code values are possible. For an injection device with possible out-dosing amounts during one out-dosing event between e.g. 1 IU insulin and 80 IU insulin in increments of 1 IU a 7 bits code enables absolute coding/decoding of each increment and the frequency of reading the code may therefore be reduced to be performed only when out-dosing starts and when out-dosing stops.

The code pattern may be integrated on a moving part in multiple different ways. Examples of methods of producing detectable code patterns directly on the moving part that can be read by the optical detector/decoder system are: Printing on the moving part with different colours or tones of grey scale; providing areas on the moving part with dark tone and/or other areas with bright tone e.g. by means of printing, embossing or laser marking on areas; making areas on the moving part that reflects light towards the detector (e.g. by making surface concave or parallel with detector field of view) and/or other areas that reflects light away from the detector (e.g. by making surface convex or non-parallel with detector field of view or by making a rough surface texture); making holes, cut-outs or transparent areas at locations in the moving part that allows a direct passage of light through the holes/cut-outs/transparent areas to the optical detector and no passage or reduced passage of light outside the holes/cut-outs; making areas on the moving part with special optical properties (e.g. by adding an optical filter, by polarisation or by producing areas with different absorption of light or by producing areas that ensure diffuse reflection of light); making the movable part so it consists or two (or more) components, the two (or more) components having different optical characteristics (e.g. different colours, brightness, reflection direction, filters, polarisation and/or absorption of light); making holes, cut-outs or transparent areas at special fields in the moving part that allows a direct view of the surface of another component and no passage or reduced view of the surface of the other component outside the holes/cut-outs/transparent areas (the other component may be fixed or moving), the surface of the other component having different optical characteristics than the moving part (e.g. different colours, brightness, reflection direction, filters, polarisation and/or absorption of light); a combination of two or more of the embodiments mentioned above.

FIG. 2A shows a rotatable part 200 with printed or laser marked areas 201 with dark colour and/or other areas 202 with bright colour, e.g. six areas with dark colour and six areas with bright colour. FIG. 2B shows a rotatable part 210 with areas of the structure which reflect light towards the optical detector/decoder and other areas which reflects light away from the optical detector/decoder, e.g. six areas 211 with concave surface that reflects light towards the optical detector/decoder and six areas 212 with rough surfaces that scatter or disperse light away from the optical detector/decoder.

The code pattern may be placed on a continuous surface of the moving part, or it may be segmented onto multiple broken surfaces of the moving part. If the code pattern is placed on multiple broken surfaces of the moving part, additional optical detectors/decoders may be needed. FIGS. 3A and 3B illustrate the principle of placing the code pattern on multiple broken surfaces 221 on a part 220 that moves linearly, such a system comprising two optical detectors/decoders 222, 223 securing that at least one detector/decoder will capture the moving code pattern. FIGS. 4A and 4B illustrates the principle of placing the code pattern on multiple broken surfaces 231 on a part 230 that rotates, such a system also comprising two optical detectors/decoders 232, 233.

The code pattern may be designed in multiple different ways. Examples of code patterns that can be read by an optical detector/decoder system are: Binary codes, i.e. codes with radix 2, e.g. designed as a code based on the binary number system, or as a binary-reflected Gray-code. A binary code with more than one bit may be produced by multiple code tracks, or by a single code track with multiple optical detectors/decoders, e.g. by the principle of quadrature encoding, or by a combination hereof; analogue (non-discrete) codes, e.g. designed as a grey scale code or as a colour tone code.

Between the optical detector/decoder and the moving part with the code pattern there may be an unobstructed passage of light or the passage of light may be limited by other structures e.g. a housing or a label material which is especially relevant in system designs where the moving part is integrated in the injection device itself and the optical detector/decoder is incorporated in an add-on device. In such instances the structure between the moving part with the code pattern and the optical detector/decoder can be modified by having an opening in the structure, or the material characteristics for the structure (e.g. a housing or a label) between the moving part with the special code pattern and the optical detector/decoder may be selected so it is sufficiently transparent for light to enable detection by the optical detector/decoder. The transparency may be limited to only relevant wave lengths, possibly being non-visual for the normal human eye. Alternatively an add-on device may contain a system that penetrates the structure (e.g. a housing or a label) between the moving part with the code pattern and the optical detector/decoder before the time of detection, e.g. during mounting of the add-on device on or in the injection device. Alternatively a mechanical part, e.g. a lid, could be opened or removed from the device by the user.

If the optical detector/decoder is integrated in an add-on device to be mounted on or in the injection device, the moving part with the code pattern may either be an integrated part of the injection device, or it may be an integrated part of the add-on device. If the coded moving part is an integrated part of the add-on device, the coded moving part must be connected to a moving part of the out-dosing mechanism in the injection device, e.g. by use of a mechanical interface, e.g. gear wheels and/or belt drives.

The out-dosing amount data acquisition system additionally comprises a triggering system that defines the relevant time for the optical detector/decoder to read the special code pattern on the moving part. For example, the system may comprise a mechanically actuatable electro-mechanical switch detecting the position of a moving part of the out-dosing activation mechanism in the injection device, e.g. a user actuated push button and/or an element which position is related to the position or state of the user actuated push button. For example, an electromechanical switch may detect when the out-dosing activation mechanism is in a state immediately before the actual out-dosing starts (corresponding to the above-described intermediate position), and immediately after the out-dosing stops. When activated the optical detector/decoder reads the code pattern on the moving part immediately before the actual out-dosing starts, and immediately after the out-dosing stops, and optionally also a number of times in the time period between start and stop of the actual out-dosing. Based on these readings the out-dosed amount of drug can be calculated.

Alternatively, the system comprises an optical trigger system comprising one or more optical detectors that detect when the injection device is about to enter the out-dosing state. The detection of whether the injection device is in the out-dosing state may be performed by means of an optical detector that detects the position of a moving part of the out-dosing mechanism (and/or of a part which position is related to the position or state of a part of the out-dosing mechanism) and/or of a moving part of the out-dosing activation mechanism in the injection device, e.g. a user actuated push button and/or a part which position is related to the position or state of the user actuated push button. For example, the optical detector may detect when the out-dosing activation mechanism is in a state immediately before the actual out-dosing starts, and immediately after the out-dosing stops. Hereby a system that is similar to the abovementioned system with mechanically actuatable electromechanical switch can be provided.

In the above-mentioned system with an optical detector detecting the position of a moving part of the out-dosing mechanism or of a moving part of the out-dosing activation mechanism in the injection device, the time interval between the readings by the optical detector is set so it ensures timely start-up of the optical out-dosing detector/decoder system, to safely determine the out-dosed amount. Indeed, the energy consumption by an optical-based trigger system should be low, resulting in a low impact on the total power consumption of the total trigger and out-dosing amount acquisition system.

Figure 5A:
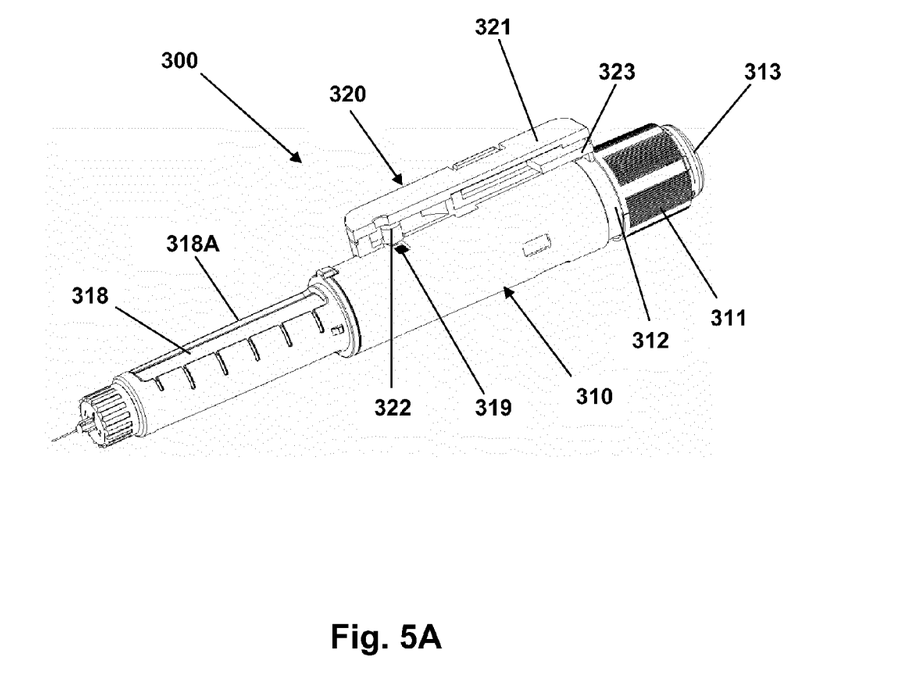
FIG. 5A shows a further embodiment of a pen-type drug delivery device in combination with an add-on dose logging module.

FIG. 5A illustrates an example of a specific embodiment of a system 300 where an add-on device 320 (shown in axial cross-section) is mounted on a pen-formed device 310, however the detection principles used could also be embodied in an integrated system. The drug delivery device comprises a rotatable dose setting member 311 and a proximally arranged release button 313 adapted to be moved between an initial position, an intermediate position, and an actuated position in which the expelling means is actuated to expel the set dose. In the distal part of the drug delivery device a drug reservoir in the form of a cartridge 318 is arranged. The cartridge holder 318A may be permanently fixed to the pen housing as in a pre-filled device, or it may be releasable mounted allowing a user to replace a drug cartridge.

Figure 5B:
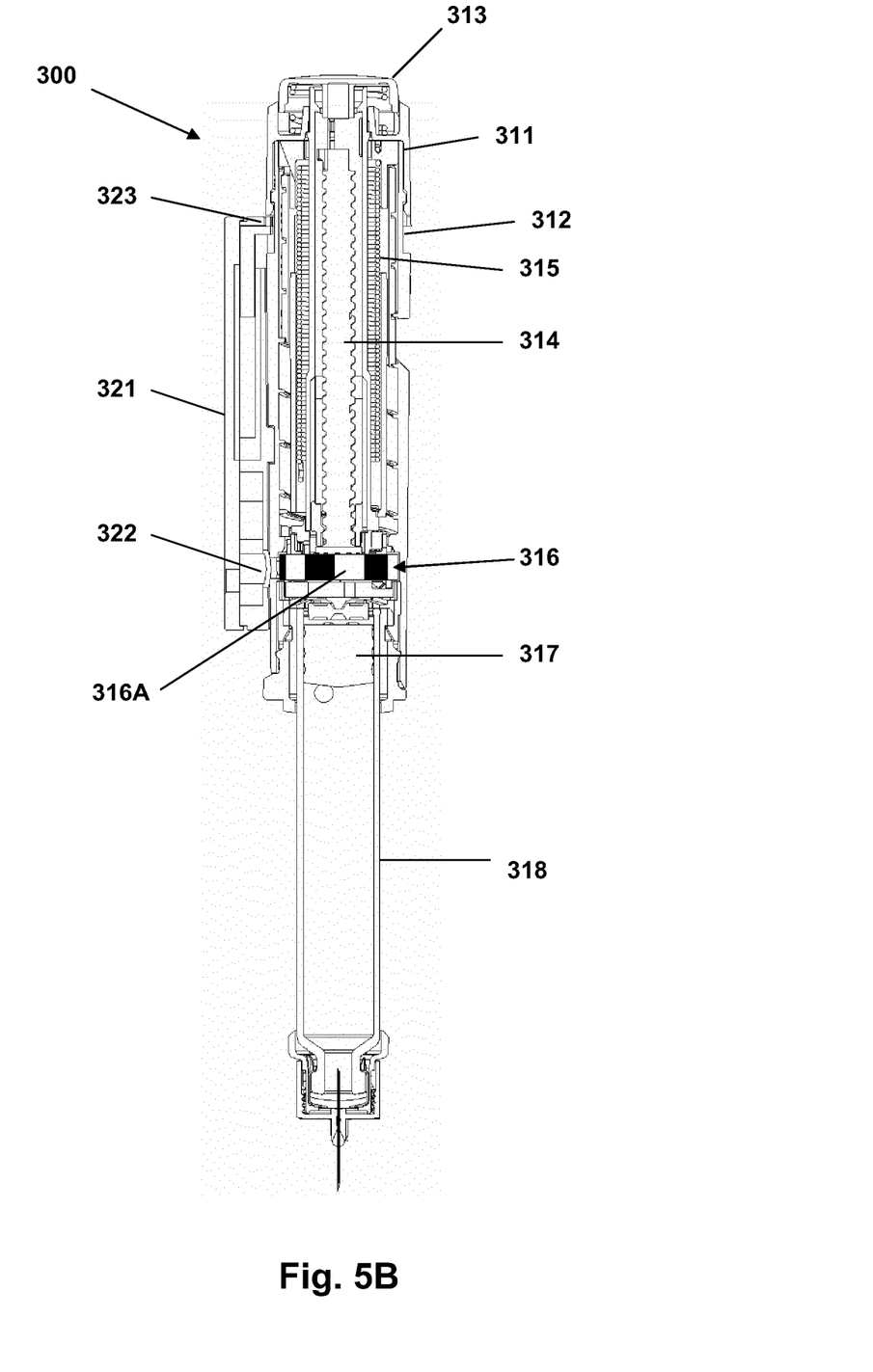
FIG. 5B shows a longitudinal cross-sectional view of the system of FIG. 5A.

The data capture unit 320 comprises a housing 321 comprising electronic detection means for capturing data representing a property related to the amount of drug expelled from the reservoir by the expelling means (see below), and switch means for initiating data capture, the switch means being actuated when the release button is moved from its initial to its intermediate position. FIG. 5B shows a longitudinal cross-sectional view of the system of FIG. 5A.

More specifically, the optical detector/decoder is an integrated part of an add-on device to be mounted on an injection device. The injection device is of the type shown in US 2008/306446 in which the expelling mechanism comprises a piston rod 314 adapted to move a piston 317 forward in a container 318, a spring 315 as well as a member 316 which is rotationally stationary during setting of a dose and the corresponding straining of the spring (e.g. by being coupled to the housing) but which can be released from this rotationally locked position when the expelling mechanism is released, this allowing the member to rotate during expelling of a dose. Typically, such a member is an "active" element serving to transfer energy from the spring strained during the dose-setting action and to the piston rod pushing the reservoir piston during expelling of a dose of drug. As described above, the expelling mechanism is released by axially depressing a proximally arranged release button, this directly or indirectly resulting in the release of a coupling allowing the mechanism to expel the set amount of drug. As also described above, the actuation of the release button between its different positions allows the detection means to be energized prior to begin of the out-dosing action per se.

As shown in FIG. 5B the rotating part 316 is an integrated part of the out-dosing mechanism in the injection device, and the angle of rotation of the rotating part is proportional with the out-dosed amount of drug, e.g. 15° rotation of the rotating part corresponds to 1 IU insulin being out-dosed. The user-actuated push button moves axially downwards when it is pushed. The movement of the user actuated push button has a mechanical coupling to an internal part of the out-dosing activation mechanism inside the injection device, which also moves axially downwards when the user-actuated push button is pressed.

In the shown embodiment an electromechanical trigger switch 323 engages, via a circumferential gap 312 between the dose dial ring 311 and the pen body, the user-actuated push button and is activated when the user pushes down the button 313. As appears, the push button serves to provide an indicator portion for actuating the switch means. When the trigger switch is activated a signal is sent to the optical detector/decoder system which subsequently starts to detect and decode the code pattern 316A printed on a rotating cylindrical ring member 316 of the out-dosing mechanism in the injection device. The optical detector/decoder 322 recognizes the optical code through an opening 319 (see FIG. 5A) in the housing of the injection device. The detection and decoding may be performed at a given frequency until the electromechanical switch is deactivated, e.g. when the user releases the user actuated push button. The code pattern on the moving part 316 is a single track code with six dark areas and six light areas as shown in FIG. 2A. Two optical detectors/decoders are placed with 15° between them, resulting in a 2 bit binary-reflected Gray-code signal by use of quadrature encoding. The value of the Gray-code changes when the rotating part has been rotated 15°. The optical detectors/decoders detect and encode the code pattern at a frequency that is fast enough to register and count every time the rotating part with the special code pattern has rotated 15°. The optical detector/decoder counts the number of times the value of the Gray-code successively has changed step by step, and hereby the out-dosing amount of drug can be calculated from the time that the electro-mechanical switch has been activated to the time that the electromechanical switch is deactivated or end of out-dosing is captured by other means.

Figure 6A:
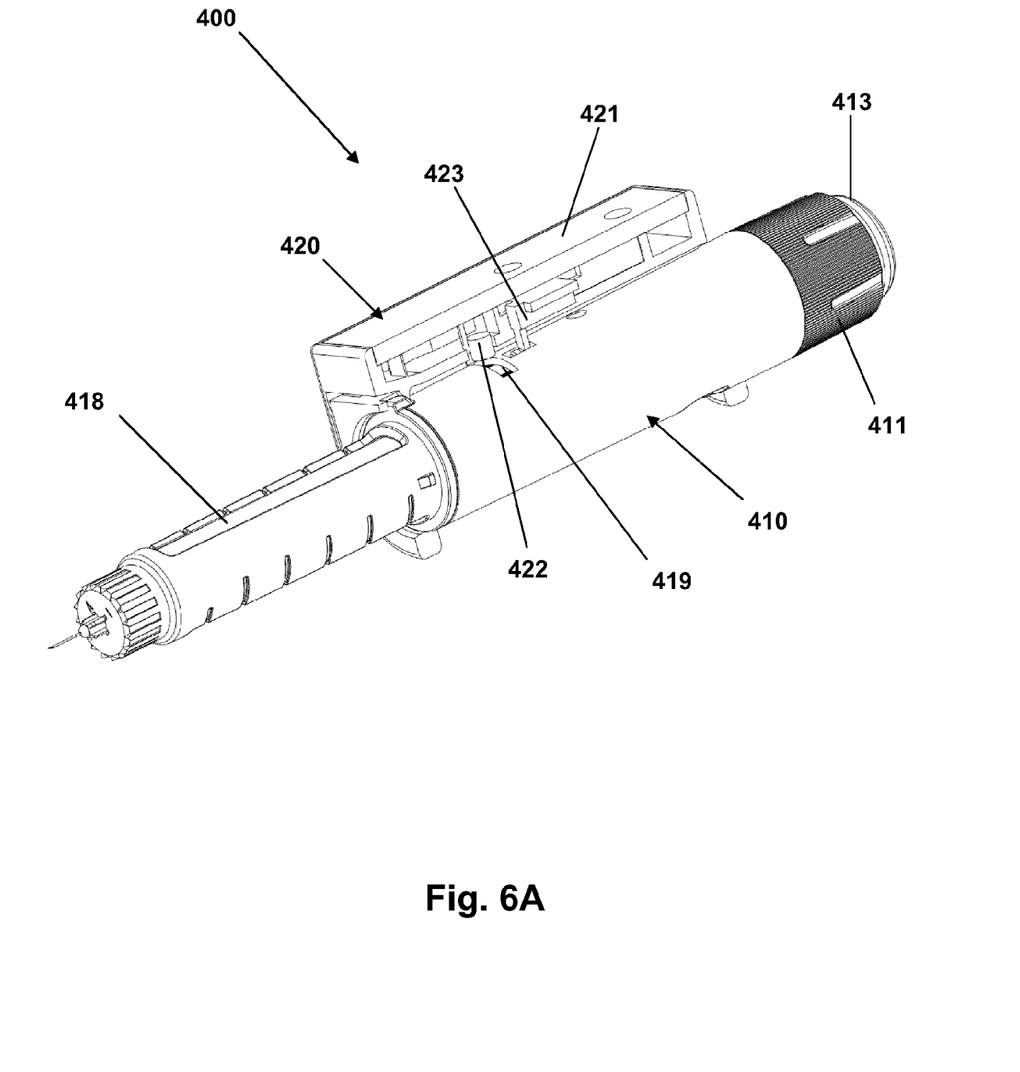
FIG. 6A shows a further embodiment of a pen-type drug delivery device in combination with an add-on dose logging module.
Figure 6B:
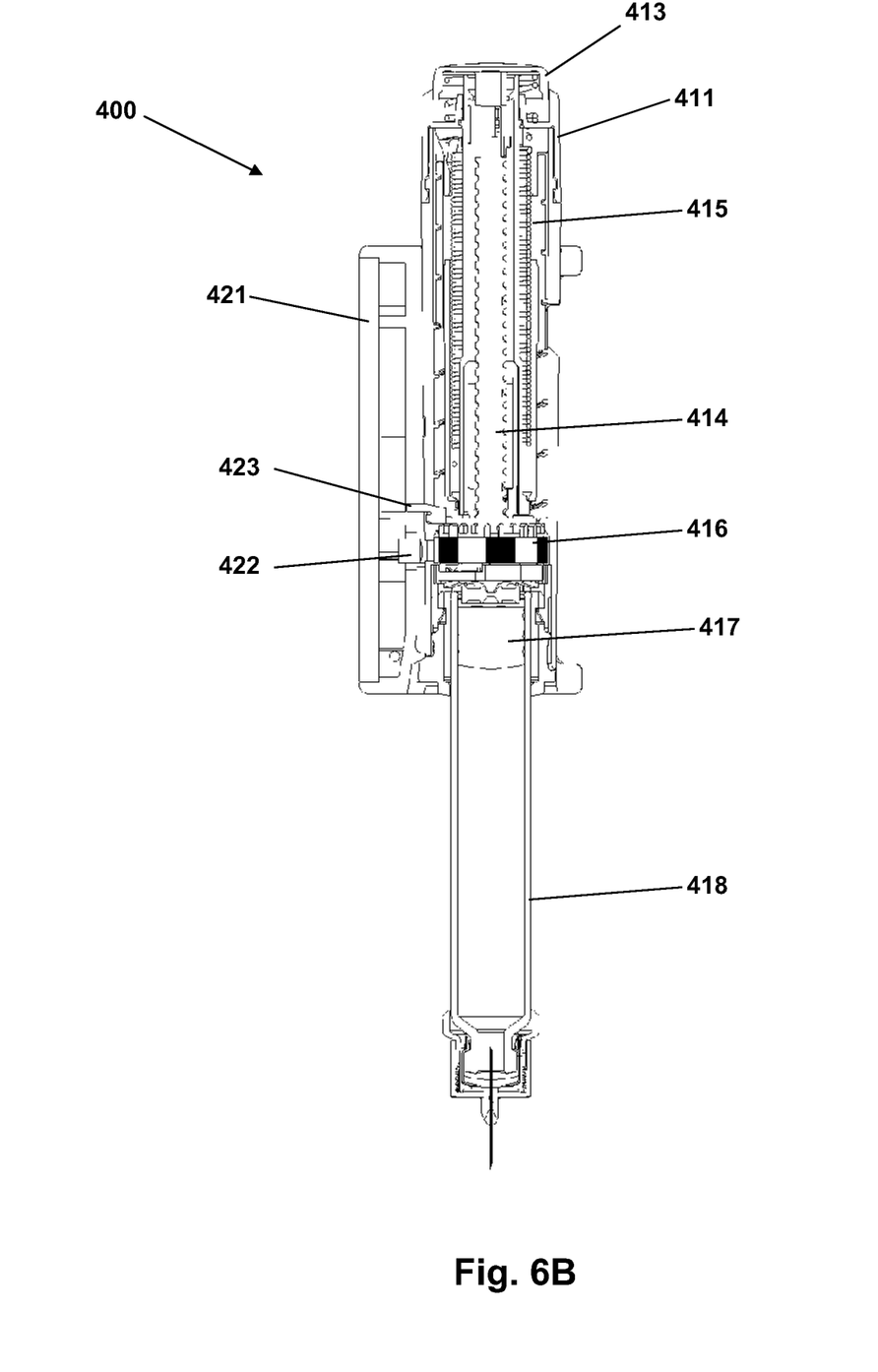
FIG. 6B shows a longitudinal cross-sectional view of the system of FIG. 6A.

FIGS. 6A and 6B illustrate in an alternative embodiment a system 400 with a pen-formed drug delivery device 410 and an add-on unit 420 in which the electromechanical trigger switch 423 is instead activated by an inner component in the injection device through an opening 419 in the housing, which movement is mechanically coupled to the user actuated push button 413 on the injection device. Apart from the circumferential gap in the FIG. 5 embodiment and the opening 412 in the FIG. 6 embodiment, the two systems of FIGS. 5 and 6 are otherwise or near-identical.

Figure 7A:
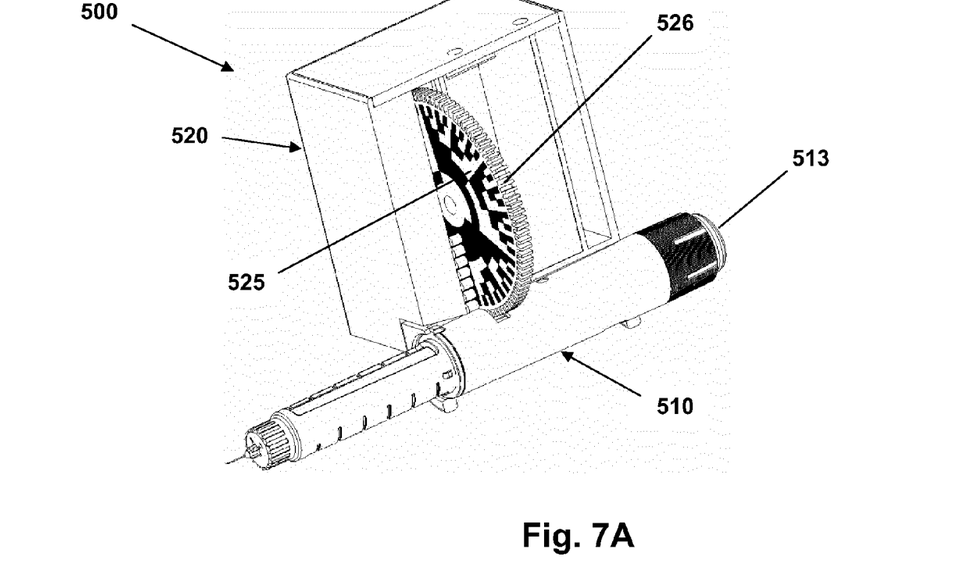
FIG. 7A shows a yet further embodiment of a pen-type drug delivery device in combination with an add-on dose logging module.
Figure 7B:
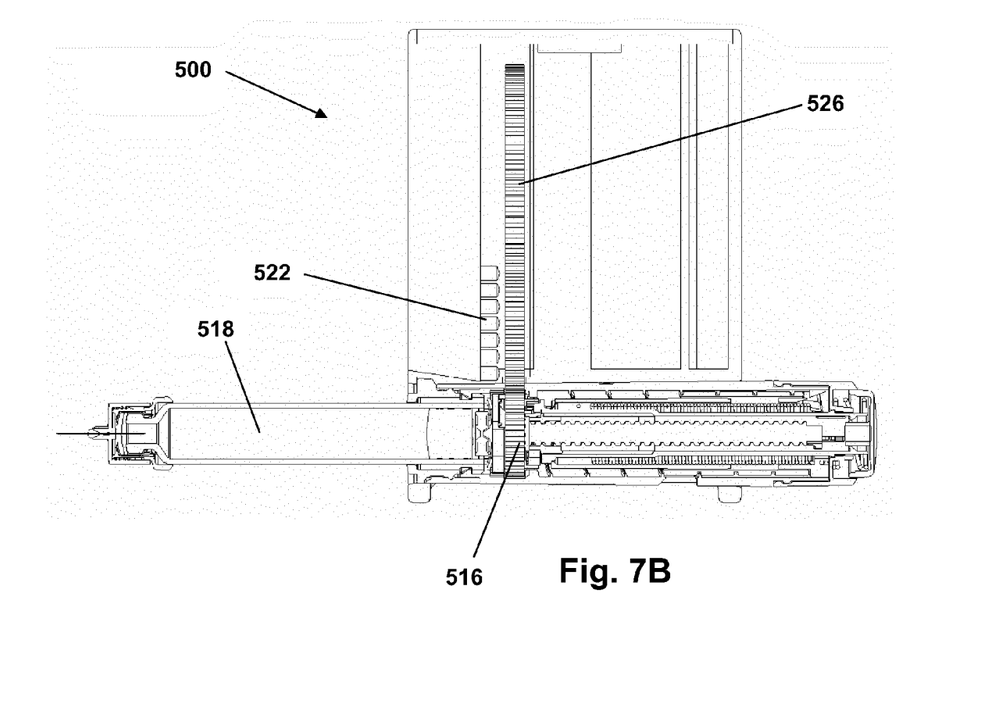
FIG. 7B shows a longitudinal cross-sectional view of the system of FIG. 7A, FIGS. 8A, 8B and 8C show in schematic representations further embodiments of an encoder/decoder system.

FIGS. 7A and 7B illustrate a further embodiment of a system 500 in which the optical detector/decoder is an integrated part of an add-on device 520 to be mounted on an injection device 510 of the same general design as the embodiments of FIGS. 6 and 7, i.e. having a part 516 that rotates proportionally with a given member of the expelling mechanism during out-dosing of the drug, the part being released by a push button 513 that the user presses in order to activate the out-dosing mechanism in the injection device.

More specifically, in the FIGS. 7 embodiment a code pattern 526 is printed on a cylindrical "code wheel" 525 formed as an integrated part of the add-on device. The code wheel rotates due to a mechanical coupling, e.g. gear wheel, to a rotating part 516 of the out-dosing mechanism in the injection device. The value of the code pattern changes every time the rotating part of the out-dosing mechanism has rotated e.g. 15° corresponding to 1 IU. The add-on device contains a trigger system as described above (not shown) that detects when the user actuates the release button and thus initiates data capture. Due to a gearing between the rotating part of the out-dosing mechanism in the injection device and the code wheel, the angular movement of the code wheel is reduced compared to the angular movement of the rotating part of the out-dosing mechanism in the injection device, e.g. the gearing may be 1 to 4. Hereby all possible out-dosing amounts between 0 IU insulin to 95 IU insulin may be registered during less than 1 full rotation of the code wheel, every increment (corresponding to 3.75° on the code wheel) thus having a dedicated "absolute" code value, this in contrast to the above relative detection mode. Hereby the out-dosed amount of drug can be calculated based on an end-reading from the previous out-dosing. Thus, alternatively, the triggering action could be based on initial capture of dose wheel movement, the determination of the out-dosed amount being based on the "absolute" position of the dose wheel at the end of the out-dosing action, e.g. either based on a triggering action or by a determination that the dose wheel has not moved for a given amount of time. Indeed, such a system would necessitate a data capture system having low energy consumption in sleep mode as no separate wake-up triggering would be provided.

Figure 8A:
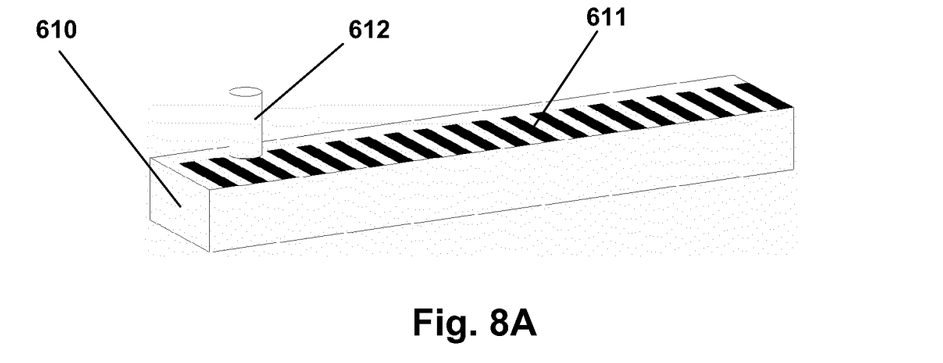
Figure 8B:
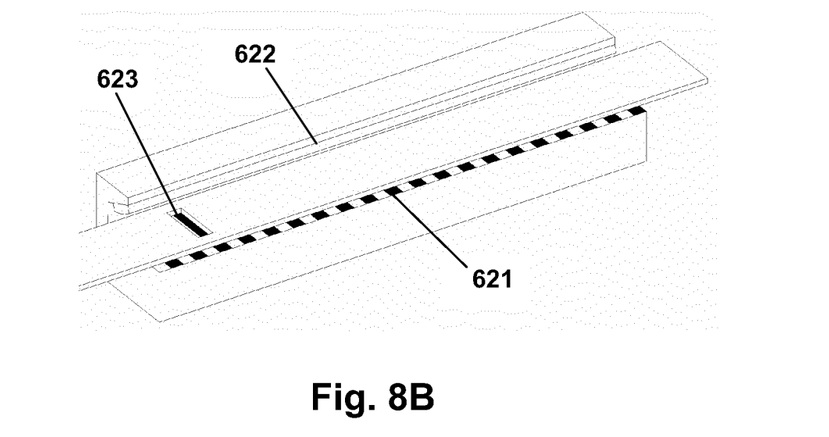
Figure 8C:
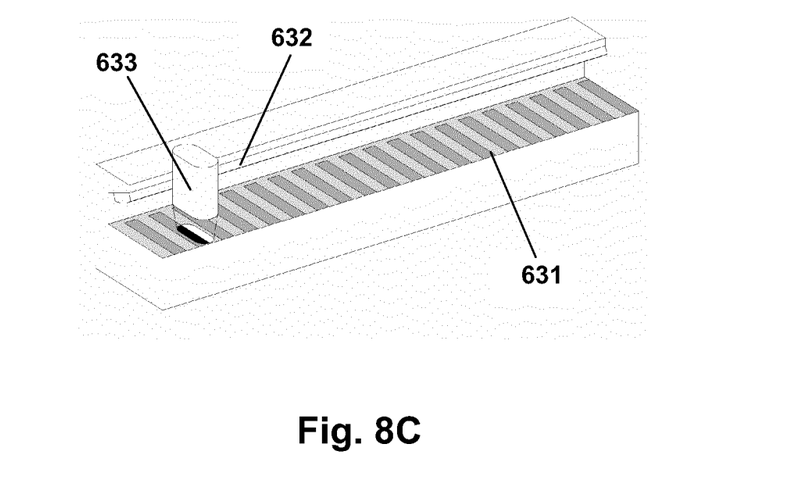

The above-described embodiments are based on an arrangement in which the optical detector/decoder is fixed and the moving part with the code pattern moves relative to the detector. Alternatively as shown in FIGS. 8A-8C the code pattern 611 could be fixed, e.g. printed on the device housing 610, and the optical detector/decoder 612 could move relative to the code pattern. For such an arrangement the optical detector/decoder could be physically connected, e.g. by a mechanical connection, with a moving part of the out-dosing mechanism.

As a further alternative (see FIGS. 8B and 8C) both the code pattern 621, 631 and the optical detector/decoder 622, 632 may be fixed. The field of view of the optical detector/decoder contains the entire code pattern, but it is only possible to read the code pattern for a specific area of the code. A third movable element (e.g. a frame 623 or a light source 633) defines the readable area and moves during out-dosing. For such embodiments the third movable element that defines the readable area would be connected with a moving part of the out-dosing mechanism.

Figure 9A:
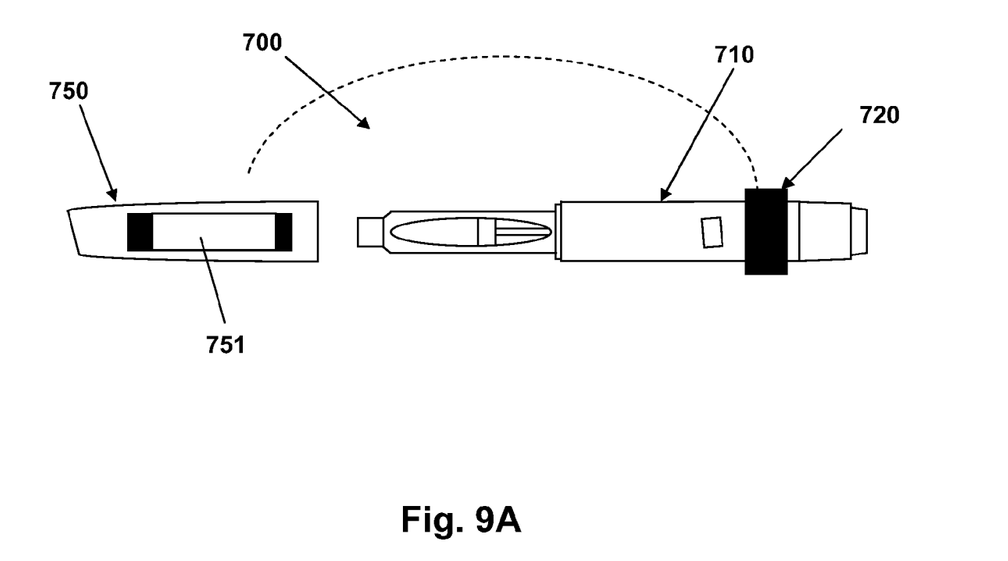
FIG. 9A shows an embodiment of a pen-type drug delivery device in combination with a two-part add-on dose logging system.
Figure 9B:
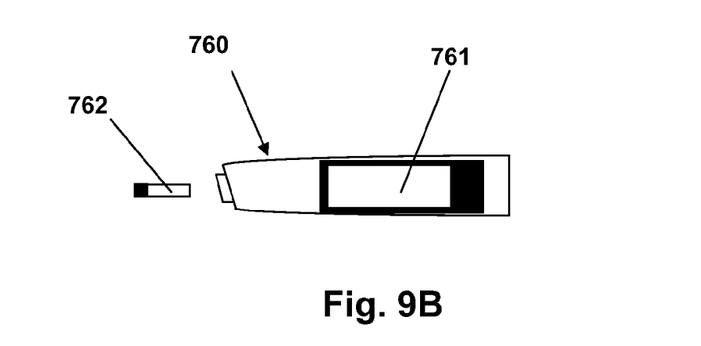
FIG. 9B shows an embodiment of a BGM cap unit for a pen-type drug delivery device of the type shown in FIG. 9A.

With reference to FIGS. 9A and 9B an alternative configuration for a drug delivery system with data capture means will be described. More specifically, the system 700 comprises a pen-formed drug delivery device 710 and an add-on assembly provided as two units, one unit 720 containing the data capture means and adapted to be coupled to the pen body, and one unit 750 containing an electronic display 751, the latter also serving as a cap for the drug deliver device. The two parts have means to communicate with each other (by wire or wirelessly) whereby the add-on display part is able to display information sent to it from the add-on device part. The display may be in the form of a flexible tag device comprising no battery (i.e. electrochemical cell) with receiving means adapted to receive RF signals also used to energize the display controller. The display may be based on mono-chromatic or colour e-ink paper or another bi-stable display technology.

The display part can be an autonomous accessory device in itself with its own self-contained functions, e.g. a blood glucose meter (BGM) in a pen cap 760 adapted to receive BG test strips 762, and adapted to communicate with an add-on accessory on or in an injection device (or alternatively integrated into a pen body) in order to receive data and display information based on these on its electronic display 761.

The pen cap may have other functions, e.g. a pen cap with an electromechanical interface and electronics able to sense if it has been dismounted from the pen and a display to show derived information thereof. When such an accessory device is used together with an add-on module on the device the two parts have means to communicate with each other whereby the display accessory part is able to display information sent from the injection devices add-on device part on its electronic display.

In the above description of exemplary embodiments, the different structures and means providing the described functionality for the different components have been described to a degree to which the concept of the present invention will be apparent to the skilled reader. The detailed construction and specification for the different components are considered the object of a normal design procedure performed by the skilled person along the lines set out in the present specification.

The invention claimed is:

1. A drug delivery system, comprising:
an expelling device for expelling an amount of drug from a reservoir, comprising:
a setting device allowing a user to set a dose amount of drug to be expelled, and
an actuation device for releasing or driving the drug expelling device to expel the set dose amount,
an electronically controlled capturing system for capturing data representing a property related to the amount of drug expelled from the reservoir by the expelling device, and
a switch device for starting initialization of the capturing system,
wherein the actuation device comprises a push button, characterized in that the push button is adapted to be pushed distally, for said releasing or driving of the drug expelling device between:
an initial position,
an intermediate position in which the switch device is actuated to start initialization of the capturing system, and
an actuated position in which the expelling device is actuated to expel the set dose,
whereby the capturing system is allowed to initialize during the push button's movement between the intermediate position and the actuated position.

2. A drug delivery system as in claim 1, comprising a first indicator portion which moves when the push button is moved from its initial to its intermediate position.

3. A drug delivery system as in claim 2, wherein the first indicator portion is moved linearly when the push button is moved from its initial to its intermediate position.

4. A drug delivery system as in claim 2, wherein the switch device comprises an optical sensor structure adapted to detect when the first indicator portion is moved corresponding to the push button being moved to its intermediate position.

5. A drug delivery system as in claim 2, wherein the switch device comprises a mechanical switch adapted to be actuated when the first indicator portion is moved corresponding to the push button being moved to its intermediate position.

6. A drug delivery system as in claim 1, wherein the expelling device comprises an identifier associated with a second indicator portion which moves during drug expelling and represents a property related to the amount of drug expelled from a reservoir by the expelling device, the capturing system being adapted to capture the identifier.

7. A drug delivery system as in claim 6, wherein the second indicator portion moves rotationally during drug expelling.

8. A drug delivery system as in claim 6, wherein the capturing system comprises an optical sensor structure, and the identifier is adapted to be captured by the optical sensor structure.

9. A drug delivery system as in claim 6, comprising a drug delivery unit and a data capture unit releasably attachable to each other, the drug delivery unit comprising:
the drug expelling device,
the setting device, and
the actuation device,
the data capture unit comprising:
the electronically controlled capturing system, and
the switch device.

10. A drug delivery system as in claim 9, wherein
the data capture unit further comprises a transmission device for wirelessly transmitting the captured data, and
the drug delivery system further comprises a cap unit releasably mountable to the drug delivery unit, comprising:
a receiving structure for receiving the captured data from the data capture unit, and
a display device to display a value corresponding to the captured data.

11. A drug delivery system as in claim 1, comprising a drug reservoir.

12. A drug delivery system as in claim 1, the system being configured to receive a replaceable drug reservoir in the form of a drug cartridge.

13. A drug delivery system, comprising:
a drug expelling device for expelling an amount of drug from a reservoir, comprising:
a setting device allowing a user to set a dose amount of drug to be expelled, and
an actuation device further comprising a push button adapted to be pushed distally for releasing or driving the drug expelling device to expel the set dose amount,
an electronically controlled capturing system for capturing data representing a property related to an amount of drug expelled by the drug expelling device,
an identifier associated with a member which moves during drug expelling and represents a property related to the amount of drug expelled from a reservoir by the expelling device, the capturing system being adapted to capture the identifier, and
a switch device further comprises a push button for starting initialization of the capturing system, the switch device being actuated as the identifier starts to move when the drug expelling means has been released or starts to be driven by the actuation device,
wherein dose data representing a property related to the amount of drug expelled from the reservoir by the expelling means is captured when the set dose amount has been expelled or expelling has stopped for a predetermined amount of time.

14. A drug delivery system as in claim 13, wherein the identifier is used for both actuation of the switch device and capturing of dose data.

15. A drug delivery system as in claim 13, wherein
the capturing system comprises an optical sensor device, and
the identifier is adapted to be captured by the optical sensor device.

* * * * *